United States Patent [19]

Hurley et al.

[11] Patent Number: 4,997,842

[45] Date of Patent: Mar. 5, 1991

[54] METABOLITES OF PIRMENOL

[75] Inventors: Timothy R. Hurley, Ypsilanti; Dino A. Sherwood, Taylor; Peter W. K. Woo, Ann Arbor, all of Mich.; Karl-Otto Vollmer, Freiburg, Fed. Rep. of Germany; Egmont Schaller, Heuweiler, Fed. Rep. of Germany; Wolfgang Klemisch, Freiburg, Fed. Rep. of Germany; Albrecht V. Hodenberg, Kenzingen, Fed. Rep. of Germany

[73] Assignee: Warner-Lambert Co., Morris Plains, N.J.

[21] Appl. No.: 476,868

[22] Filed: Feb. 8, 1990

[51] Int. Cl.$^5$ .................... A61K 31/44; C07D 401/06; C07D 211/70

[52] U.S. Cl. ................... 514/332; 514/357; 546/266; 546/333

[58] Field of Search .............. 514/332, 357; 546/266, 546/333

[56] References Cited

U.S. PATENT DOCUMENTS 4,112,103  9/1978  Fleming .............. 514/318

OTHER PUBLICATIONS

CA 97(11):92158m.

Primary Examiner—Mary C. Lee
Assistant Examiner—Jacqueline Haley
Attorney, Agent, or Firm—Joan Thierstein

[57] ABSTRACT

The present invention relates to the + or − pirmenol stereoisomers and to selected metabolites of pirmenol or (+,−)-cis-α-[3-(2,6-dimethyl-1-piperidinyl))propyl]-α-phenyl-2-pyridinemethanol which are active as antiarrhythmic agents. The pharmacological use of the metabolites that is the present invention is as antiarrhythmic agents. Pharmaceutical compositions comprising the metabolites are also within the scope of the invention.

14 Claims, No Drawings

METABOLITES OF PIRMENOL

BACKGROUND OF THE INVENTION

The present invention relates to selected metabolites of pirmenol, i.e., (+,−)-cis-α-[3-(2,6-dimethyl-1-piperidinyl)propyl]-α-phenyl-2-pyridinemethanol or N-[4-phenyl]-4-(2-pyridyl)-4-hydroxybutyl]-cis-2,6-dimethylpiperidine. The pharmacological activity of both pirmenol and the metabolites that are the present invention is antiarrhythmia. Thus, pharmaceutical compositions and use therefor comprising an antiarrhythmic effective amount of the metabolites are also within the scope of the invention.

Pirmenol is the starting material for synthetic preparation of the present invention metabolites. Therefore, U.S. Pat. No. 4,112,103, describing pirmenol, is incorporated by reference herein.

Precursors for pirmenol are disclosed in CA 97(11):92158m. These include α-[3-(2,6-dimethyl-1-piperidinyl)-1-propenyl]-α-phenyl[1(Z),2α,6α]-2-pyridinemethanol and α-[3-(2,6-dimethyl-1-piperidinyl)-1-propynyl]-α-phenyl[1(Z)-2α,6α]-2-pyridinemethanol. These disclosed precursors are different from the present invention because each precursor includes an unsaturated hydrocarbon chain. Also, the present compounds differ from both pirmenol and these precursors in the 2,6-dimethylpiperidine moiety.

SUMMARY OF THE INVENTION

The present invention relates to a novel compound and its interconverting form or mixtures thereof having an antiarrhythmic utility. The present invention compound, its interconverting form and mixture thereof are now in purified form not heretofore available. The invention also relates to a method for treating cardiac arrhythmia using the compound, interconverting form or mixtures thereof, and to pharmaceutical compositions comprising the compound, its interconverting form or mixtures thereof for treating cardiac arrhythmias together with a pharmaceutically acceptable carrier.

Specifically, the present invention relates to a compound of the formula (Ia)

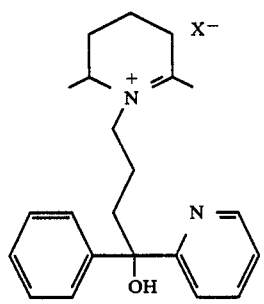

Ia or its interconverting form (Ib)

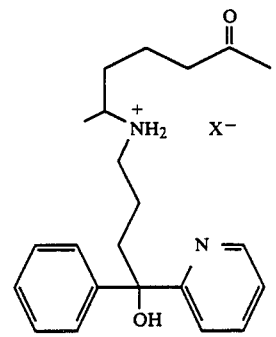

Ib mixtures thereof, or individual stereoisomers thereof wherein X is a pharmaceutically acceptable anion; and pharmaceutically acceptable salts thereof.

Forms Ia and Ib may be found as a mixture in the solid state, as indicated by IR absorption at 1662 and 1710 cm$^{31\ 1}$, respectively, and supported by elemental analyses.

In aqueous solution at pH 3, two peaks are detected by high pressure liquid chromatography (HPLC) using a silica gel column, a minor peak with low retention time and a major peak with high retention time. Isolation of each peak and reinjection give rise to the same two peaks. Reduction studies with cyanoborohydride or borohydride showed that the fast, minor peak corresponded to the keto form, Ib, and the slow, major peak, to the imine form, Ia.

The keto form, Ib, is characterized by $^{13}$C peak at about 205 to 220 ppm and the imine form, Ia, about 190 to 195 ppm. The proton nuclear magnetic resonance (NMR) peak of the C-methyl group (the one remote from the interconverting carbon atoms) appears at slightly lower field for Ia, compared to that for Ib.

The present invention may also include the following form Ic (see Scheme 1 below), which may result from deprotonations of Ia:

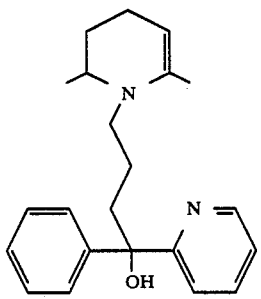

Ic

From pH 4 to 10.5 the composition appears to be relatively unchanged as compared to pH 3, except that the iminium form, Ia, (193 ppm) is increasingly dominant at the higher pH.

Above pH 10.5 the free base of Ib starts to oil out from aqueous solution because of insolubility. However, as a solution in chloroform, the oil consists mainly as the ketone Ib, as indicated by infrared (IR) absorption at 1710 cm$^{-1}$ and $^{13}$C absorption at 208 ppm.

The ketone free base is transformed to a cyclic enamine form (that appears to be of the formula Ic) under high vacuum (about 10$^{-7}$ torr) and temperature of about 106° C. in the mass spectrometer, as indicated by M-18 peak of 336.

The free base, when dissolved in organic polar solvent like methanol-water mixture, showed a very weak ketone peak in $^{13}C$ NMR at 218 ppm.

Other embodiments of the present invention include pharmaceuticals for the treatment, by a compound Ia, Ib, mixtures thereof, or pharmaceutically acceptable

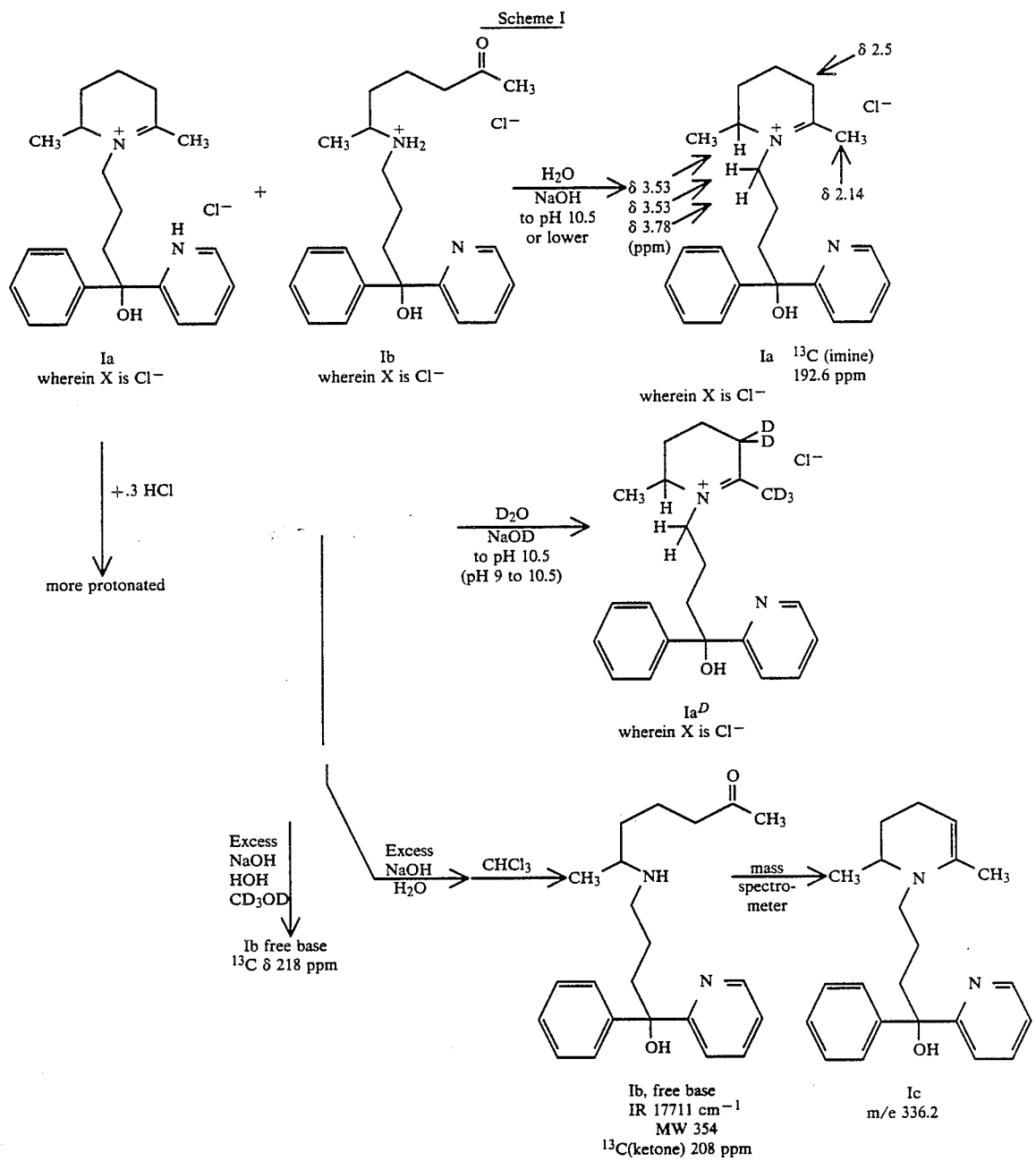

Finally, the invention is the isolated metabolite of the formula Ia, the interconverting form Ib, and mixtures thereof which is obtained from the urine of a dog to which pirmenol is administered. Isolation is achieved by extraction with an organic solvent followed by purification using HPLC.

The isolated metabolite Ia and its interconverting form Ib are identical to that obtained from synthesis by chemical means described hereinafter.

The present invention is also cis-(+)-α-[3-(2,6-dimethyl-1-piperidinyl)propyl]-α-phenyl-2-pyridinemethanol or cis-(+)-α-[3-(2,6-dimethyl-1-piperidinyl)-propyl]-α-phenyl-2-pyridinemethanol, i.e., the resolved enantiomers of pirmenol.

acid addition salts thereof, of arrhythmia.

A still further embodiment of the present invention is the preparation of such pharmaceutical compositions.

DETAILED DESCRIPTION OF THE INVENTION

The present invention relates to the compound and its interconverting forms of the formula Ia and Ib, and mixtures thereof and pharmaceutically acceptable salts thereof. The forms are antiarrhythmic agents so the invention relates to a method of treating arrhythmia in humans suffering therefrom comprising administration of the compound of the formula Ia, its interconverting forms, Ib, or mixtures thereof and pharmaceutically acceptable acid addition salts thereof in unit dosage form. The present invention thus also relates to pharmaceutical compositions for treating arrhythmias comprising an antiarrhythmic effective amount of the compounds of formula Ia, Ib or mixtures thereof and pharmaceutically acceptable acid addition salts thereof together with a pharmaceutically acceptable carrier.

The anion shown as X above is selected from those known to an ordinarily skilled artisan and may be the anion from strong inorganic acids such as hydrochloric acid, perchloric acid, hydrobromic acid, sulfuric acid, and the like, or organic acids such as acetic acid, trifluoroacetic acid, methanesulfonic acid, and the like. The preferred anion is chloride.

Likewise, the acid addition salts are those known by artisans to form from acids such as HX. These are understood to be further protonated forms of Ia and Ib.

The compounds of the invention may be as represented by formula Ia or Ib, their further protonated forms, or in the free base forms as derived by means shown in Scheme I above. Each of these forms depends on suitable adjustment of the pH of the composition as an isolated or solvated product within the skill of an ordinary artisan.

The compounds of the invention can also exist in anhydrous form as well as in solvated, including hydrated form.

In general, the free bases and the salt forms may differ in their physical form or solubility properties but are otherwise equivalent for the purposes of the invention.

Likewise, in general the hydrated forms and the solvated forms with pharmaceutically acceptable solvents are equivalent to the anhydrous or unsolvated form for the purposes of the invention.

Synthesis of the compounds of the present invention is generally analogous to the Leonard method described in Fieser and Fieser, *Reagents for Organic Synthesis*, Vol. 1, pp. 647 and 652, footnotes 13 and 14 to N. J. Leonard, et al, Am. Soc., 77, 439 (1955) and N. J. Leonard, et al, Am. Soc. 78, 3457 (1956), which are both incorporated by reference. Starting materials are either known or available from preparations analogous to those known in the literature. These starting materials are meant to include pirmenol as disclosed in U.S. Pat. No. 4,112,103 and each of the isolated and purified stereoisomers, i.e., + or − form of pirmenol or cis-α-[3-(2,6-dimethyl-1-piperidinyl)propyl]-α-phenyl2-pyrimidinemethanol or its hydrochloride salt. Each R and S isomer of the compounds of the, present invention is prepared by resolution of the mixture reported in U.S. Pat. No. 4,112,103 noted above. The resolution is described in Example 2 hereinafter. The (−)-(cis)-α-[3-(2,6-dimethyl-(-piperidinyl)propyl]-α-phenyl-2-pyrimidinemethanol is characterized by the rotation data:

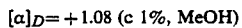
$[\alpha]_D = +1.08$ (c 1%, MeOH)

The (+) form is characterized by rotation data:

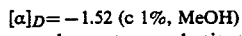
$[\alpha]_D = -1.52$ (c 1%, MeOH)

The carbon atom substituted by the hydroxyl moiety of the present compound of formulas Ia or Ib is also asymmetric. Both rotatory forms are thus also the present invention as well as mixtures of the individual isomers. The compounds of the present invention that are individual R and S isomers may be synthetically prepared from the starting material having the appropriate precursor R and S form obtained by resolution techniques as described herein from the pirmenol in U.S. Pat. No. 4,112,103.

One of skill in the art would also recognize the compounds of the invention may contain other asymmetric carbon atoms. Thus, the invention is meant to include additional stereoisomers and mixtures thereof. Such individual isomers may be prepared or isolated by methods known in the art.

Pharmaceutically acceptable salts of the present invention compounds Ia and Ib and their mixtures are prepared by procedures within that known to the skilled artisan for the preparation of acid addition salts.

The structures of the compounds of the present invention are established by elemental analyses, mass spectrometry, infrared spectrometry, $^{-}C$ and $^1H$ nuclear magnetic resonance spectroscopy, ultraviolet spectroscopy, and chemical transformation to suitable derivatives by chemical means and subsequent analyses of such derivatives. The data from such studies have been partially shown in Scheme I above.

The compounds of the invention are new chemical compounds or now newly purified compounds of value as pharmacological agents. More specifically, these compounds are antiarrhythmic agents. The activity of these compounds is shown by the antiarrhythmic screen reported in *Circulation* 1, 1318 (1950), as described in U.S. Pat. No. 4,112,103, which is also, therefore, incorporated by reference for this description. The compounds are tested intravenously 19 to 24 hours after coronary artery ligation, and the degree of effectiveness is determined by the degree of conversion of ventricular ectopic beats to sinus beats.

The table shown below gives the results of the screen performed on 2,3,4,5-tetrahydro-1-[4-hydroxy-4-phenyl-4-(2-pyridinyl)butyl]-2,6-dimethylpyridinium chloride (Ia) hydrochloride and its interconverting 6-[[4-hydroxy-4-phenyl-4-(2-pyridinyl)butyl]amino]6-methyl-2-hexanone hydrochloride (Ib), or 1-methyl-5-oxohexylamine (Ib), hydrochloride, which has been equilibrated in aqueous solution for at least 5 hours, at which time HPLC indicates a constant ratio of 12.5 between the major and minor components and a combined purity of 99%.

TABLE

| Compound | Dose | Time Post Dose | % Conversion |
|---|---|---|---|
| Pirmenol | 5 mg/kg IV | End dose | 92 |
|  | (n = 4) | 5 min | 86 |
|  |  | 20 min | 61 |
|  |  | 55 min | 34 |
| Metabolites (Ia + Ib)[b,c] | 5 mg/kg IV (n = 4) | End dose | 66 |
|  |  | 5 min | 100 |
|  |  | 20 min | 100 |
|  |  | 55 min | 97 | n = number of animals tested.
[a]Dose calculated as free base, tested as salts.
[b]Activity of the metabolites is tested after allowing the solution to equilibrate at least 12 hours.
[c]Ratio of major to minor peak area is 12.5 under chromatographic conditions as follows:
Dupont Zorbax TMS reversed phase HPLC column, 5 μ, 25 cm × 4.6 mm I.D.
Mobile Phase: 0.025 M ammonium phosphate (pH 3): acetonitrile (70:30)
Flow Rate: 1 mL/min
UV Detection: 261 nm
Temp: 21°C.
Inject: 10 μL of a 0.86 mg/mL solution of Ia and Ib Correspondingly, the present invention relates to pharmaceutical compositions and methods employing the compounds of the present invention including the Ia and Ib form and pharmaceutically acceptable acid addition salts thereof, particularly the equilibrated mixture of the above assay.

More particularly, 2,6-dimethyl-2,3,4,5-tetrahydro-1-[4-hydroxy-4-phenyl-4-(2-pyridinyl)butyl]pyridinium chloride, hydrochloride, Ia and its salt, and its corresponding 6-[[4-hydroxy-4-phenyl-4-(2-pyridinyl)butyl]amino]-6-methyl-2-hexanone hydrochloride, Ib, and its salt or 1-methyl-5-oxohexylamine, hydrochloride, Ib and its salt, in the mixture as an equilibrated solution, are highly useful in controlling cardiac arrhythmias in mammals, particularly humans, when administered in amounts ranging from 0.1 to about 10 mg per kg of body weight per day, and such dosage units are employed so that a total of from about 7 to about 700 mg of active ingredient for a subject of about 70 kg body weight are administered in a 24-hour period, preferably in divided doses. A preferred dosage regimen employs a range of from 1 to 5 mg of active ingredient per kg of body weight per day and wherein the total daily dosage is divided into four units and each taken after an appropriate time interval.

The compounds of the present invention may be administered by any convenient route such as orally, intraperitoneally, subcutaneously, intramuscularly or intravenously.

Compositions according to the present invention having the desired clarity, stability, and adaptability for parenteral use are obtained by dissolving from 0.1 to 10.0% by weight of active compound in a vehicle such as water, a polyhydric aliphatic alcohol or mixtures thereof. In addition to water, especially satisfactory are glycerin, propylene glycol, and the polyethylene glycols. The polyethylene glycols consist of a mixture of nonvolatile, normally liquid, polyethylene glycols which are soluble in both water and organic liquids and which have molecular weights of from about 200 to about 1500. Although the amount of active compound dissolved in the above vehicle may vary from 0.10 to 20.0% by weight, it is preferred that the amount of active compound employed be from about 1.0% to about 10.0% by weight. Although various mixtures of the aforementioned nonvolatile polyethylene glycols may be employed, it is preferred to use a mixture having an average molecular weight of from about 200 to about 400.

In addition to the active compounds, the parenteral solutions of the present invention may also contain various preservatives which may be used to prevent bacterial and fungal contamination. The preservatives which may be used for such purposes are, for example, benzyl alcohol, myristyl-gamma-picolinium chloride, phenyl mercuric nitrate, benzoalkonium chloride, phenethyl alcohol, p-chlorophenyl-α-glycerol ether, methyl and propyl parabens, and thimerosal. As a practical matter it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

The preferred concentration of active compound is 1 to 50 mg/mL of the finished compositions when intramuscular injection is the purpose for which the compositions are intended. They are equally adapted to intravenous administration when diluted with water or diluents employed in intravenous therapy such as isotonic glucose in appropriate quantities. For this use, initial concentrations down to about 0.5 to 25 mg/mL of active compound are satisfactory. They are also adapted to oral administration when diluted with drinking water.

The active compounds of the present invention may be orally administered, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions syrups, wafers, chewing gum, and the like. Such compositions and preparations should contain at least 0.1% of active compound. The percentage in the compositions and preparations may, of course, be varied and may conveniently be between about 5 to about 75% or more of the weight of the unit. The amount of active compound in such therapeutically useful compositions or preparations is such that a suitable dosage will be obtained. Preferred compositions or preparations according to the present invention are prepared so that an oral dosage salt form contains between about 1 and 200 mg of active compound.

The tablets, troches, pills, capsules, and the like may also contain the following: a binder such as gum tragacanth, acacin, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit, for instance, tablets, pills or capsules may be coated with shellac, sugar, or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically acceptable and substantially nontoxic in the amounts involved.

The compounds of Formula I are obtained by administering the antiarrhythmic compound pirmenol hydrochloride to a mammal, collecting urine from the mammal, and separating the compounds of Formula I from the urine. The compound pirmenol hydrochloride may be prepared as described in the above incorporated U.S. Pat. No. 4,112,103.

A suitable laboratory mammal from which the metabolites of the present invention can be obtained is the dog as pirmenol is intensely metabolized in the dog. The present metabolites are not known from metabolite studies in rats.

The specific procedure utilized in the present invention is to extract the urine of a dog to which the compound pirmenol hydrochloride has been administered. Chloroform is used as the extraction solvent. Evaporation of the chloroform extract gives a concentrate which is then fractionated through a series of (seven) HPLC systems applied in succession. In this manner, the compounds of Formula I are purified and isolated, and the structures are established by comparison with the equivalent compounds as synthesized in the examples hereinafter, by mass spectroscopy, ultraviolet spectroscopy, and HPLC analysis.

The following examples are provided to illustrate the methods used in the invention. They are not intended to limit the invention.

Procedures for the synthesis of the compounds of formula Ia, its interconverting form Ib, and mixtures thereof in high purity by mercuric oxidation of pirmenol free base are as follows:

Pirmenol free base is oxidized by heating with 1.25 equivalents of mercuric acetate in 5% aqueous acetic acid at 92° C., under conditions similar to those described by Leonard, et al, in "Unsaturated Amines. VIII. Dehydrogenation and Hydroxylation of 1-Methyldecahydroquinoline by Means of Mercuric Acetate", *J. Am. Chem. Soc.*, Vol. 78, p. 3463 (1956). However, since the products are not amenable to the conventional methods of purification such as distillation, crystallization, or column chromatography, isolation and purification are as follows.

Progress of the reaction is analyzed by treatment of aliquots with hydrogen sulfide and subsequent analysis by HPLC. The formation of product is accompanied by the formation of impurities, and the heating is stopped when the impurities are about up to 1%. The reaction mixture is filtered (to remove inorganic salt which presumably is mercurous acetate). The filtrate is then exhaustively extracted with an organic solvent which is capable of removing the starting material preferentially relative to the product. Solvents such as chlorinated hydrocarbons (chloroform, dichloromethane, etc), esters (ethyl acetate, etc), ethers (diethyl ether, etc), and aromatic hydrocarbons (toluene, etc) are suitable solvents. It is believed the solvents are listed in order of probable suitability.

After extraction, the aqueous phase is treated with hydrogen sulfide as described in Leonard's procedure, and the sulfides of mercury are filtered.

The filtrate, containing the products of the invention in acetate form, is then freeze-dried to a syrup to give the hydrated acetate salts. It is important not to remove all the acetate and water in order to avoid the decomposition of the products.

From the aqueous acetic solution, the products may be transformed into salts containing other anions. The amount of products present is estimated by the UV absorption at 262 nm, using a molar extinction coefficient of 7536, which is an approximate value determined empirically. The required amount of a strong acid, slightly more than one equivalent (e.g., 1.2 to 1.3) is added. The solution is then freeze-dried repeatedly until a solid is obtained.

To prepare salts of volatile acids having ionization constant similar to acetic acid, the syrup obtained from freeze drying above may be repeatedly freeze-dried from an aqueous solution of the desired acid.

A specific anion of the products may be exchanged by another by passing a solution of the salt containing the former anion through an ion exchange column containing the anions of the latter. A column containing basic functional groups like quarternary ammonium may be used. Preferably the latter anions should be those from acids having equal or stronger ionization constants than the former.

This procedure is shown in Scheme II as follows:

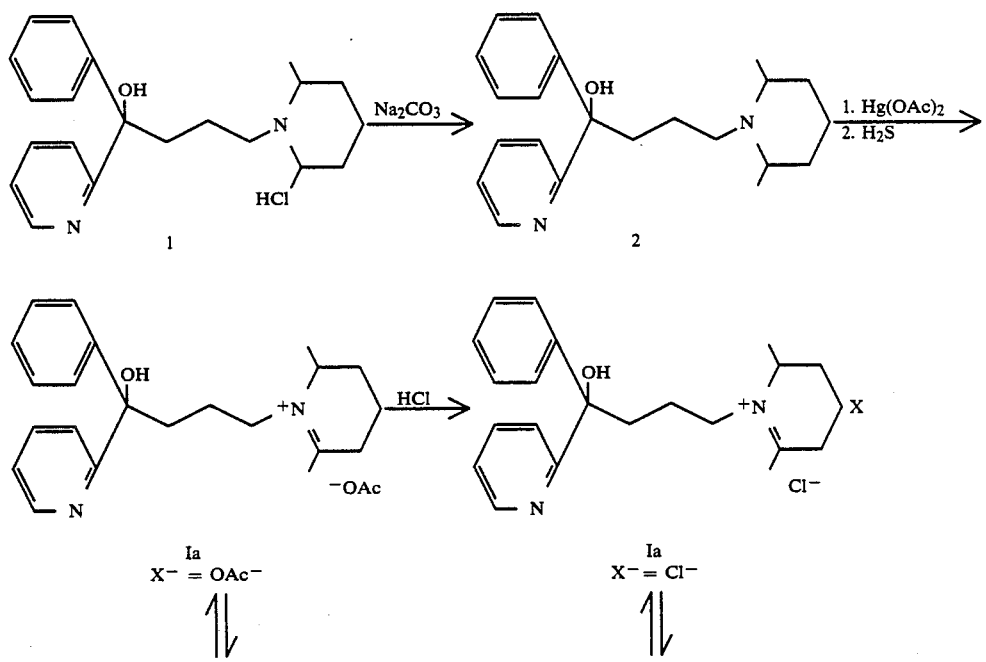

SCHEME II
Synthesis of Pirmenol Metabolite 2

SCHEME II
Synthesis of Pirmenol Metabolite 2

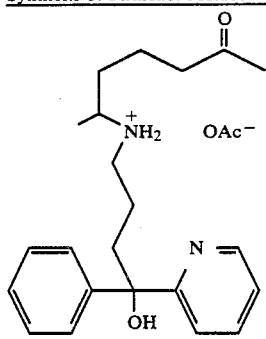

Ib
X⁻ = OAc⁻
Ia + Ib (X⁻ = OAc⁻)
3

-continued

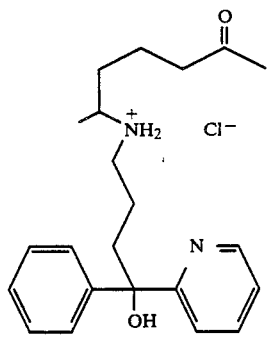

Ib
X⁻ = Cl⁻
Ia + Ib (X⁻ = Cl⁻)
4

A specific preparation is as follows:

EXAMPLE 1

A 3.6-g sample, as the acetate salt (3) is synthesized hereinafter. The acetate salt is highly unstable and also exists as an equilibrating mixture of isomers in aqueous solutions. However, this synthetic sample is clearly identical to the authentic sample extracted from the urine of a dog to which pirmenol is administered as noted above, according to MS, TLC, and HPLC. Subsequently, the more stable hydrochloride is prepared in solid form.

Conversion of pirmenol hydrochloride (1) to pirmenol free base (2).

A solution of 16.8 g of pirmenol hydrochloride in 375 mL of chloroform is washed with 60-, 25-, and 25-mL portions of 1M sodium carbonate, dried with magnesium sulfate, evaporated in vacuo, and dried in vacuo overnight to give 12.8 g (84%) of pirmenol free base (2) as a yellowish liquid.

Pirmenol metabolites which are the acetate (3) of a mixture of Ia and Ib.

A solution of the free base is heated at 92° C. with four equivalents of mercuric acetate in 5% aqueous acetic acid (1 mmole/mL). Progress of the reaction is analyzed by treatment of aliquots with hydrogen sulfide and subsequent analysis by HPLC (Alltech silica gel, 0.025M ammonium phosphate at pH 3.0:acetonitrile - 70:30). After 1.5 hours of heating, analysis shows the presence of a pirmenol metabolite 2 major component (6 minutes, 68.6%), a pirmenol metabolite 2 minor component (3.5 minutes, 6.7%), unreacted pirmenol (4.3 minutes, 24.5%), and four minor impurities (about 3 minutes, totaling 0.17%). Additional mercuric acetate solution (¼ of the original) is added, and heating is continued for another 1.5 hours. Analyses show a decrease of unreacted pirmenol to 12% but an increase of impurities to 1.06%. The reaction mixture is filtered, and the solid pressed and sucked dry. The filtrate is extracted 45 times with ½ volume portion of chloroform to remove unreacted pirmenol to a level of less than 0.5%, with simultaneous loss of some of the oxidation product, Ia and Ib mixture. Exhaustive treatment with hydrogen sulfide, filtration through glass fiber filter, and lyophilization at 0.001 mm Hg gives 8.6 g of slightly brownish liquid, the elemental analyses of which agree with the formula as shown below. The overall yield from the pirmenol hydrochloride used is 36%. Without further drying the product is kept at −20° C. to avoid rapid darkening which would otherwise occur. The compound is identical to the authentic extract from dog urine noted above according to MS, HPLC, and TLC (Rf value and tendency to turn pink on the plate soon after development; silica gel, toluene:methanol:triethylamine 92:3:5).

Anal for $C_{22}H_{28}N_2O.2.8C_2H_4O_2.0.4H_2O$ (mw 511.83): Calcd: C, 64.77; H, 7.88; N, 5.47. Found: C, 64.74; H, 8.02; N, 5.37 (average of three determinations).

As indicated by HPLC data, an aqueous solution of the product contains two isomers in equilibration with one another. However, the ratio of major to minor of the formula Ia to the formula Ib is 10 to 12 as a solution, and decreases upon lyophilization. The ratio of an aqueous solution of the lyophilized product then increases in a time-dependent manner: approximately 3.0 after 5 minutes, 8–9 after 1 hour, 12 after 4 hours, 13 after one day, and final. The ratio appears to be independent of pH from 4.0 to 10.0 after 16 days, during which much decomposition also occurs.

The equilibrating forms are represented by structures of Ia and Ib noted above.

Pirmenol derivatives Ia and Ib hydrochloride (4).

Pirmenol free base, 23.75 g (62.6 mmol) is oxidized with mercuric acetate as above. The oxidation mixture is extracted 60 times with chloroform to remove unreacted starting material giving 257 g of aqueous solution containing the oxidation product. The solution is saturated with hydrogen sulfide for 1 hour, and the mixture is filtered through glass fiber paper by suction, giving 202 g of filtrate. A small sample of the filtrate, diluted 537 times with 0.1N acetic acid, showed an absorbance of 1.769 at 264 mu. The filtrate is thus estimated to contain 25.19 mmoles of product based on a molar extinction of 7536. The filtrate is acidified to a pH of 3.4 with 33.0 mL of 1N hydrochloric acid. After dilution with water to 0.35 L, the solution is lyophilized. 1, 0.2, 1, and 0.6 L of water, in succession, to 10.5 g of the hydrochloride salt of pirmenol metabolite 2 as a light tan, extremely hygroscopic solid which is 2,3,4,5-tetrahydro-1-[4-hydroxy-4-phenyl-4-(2-pyridinyl)butyl]-

2,6-dimethylpyridium chloride, hydrochloride, and its interconverting 1-methyl-5-oxohexylamine, hydrochloride.

Anal. for $C_{22}H_{29}N_2OCl.0.31HCl.0.47H_2O$ (mw 392.7): Calcd: C, 67.28; H, 7.77; N, 7.13; Cl, 11.83; O, 5.99 Found: C, 67.34; H, 7.89; N, 7.10; Cl (inorganic) 11.76 (average of eight determinations).

The product shows a purity of more than 98.5% according to HPLC (sum of two interconverting peaks). It appears to be stable at room temperature, both as a solid (1 week, dry atmosphere) and as a 0.5% aqueous solution (1 day).

Typical HPLC chromatogram is as follows:

Instrument type: SPECTRA PHYSICIS 8700
Column Type: Econosil ™ $SiO_2$-10µ-4.6 mm × 25 cm
Solvent Description: 0.025M $NH_4H_2PO_4$,
pH 3: $CH_2CN$-70:30
Detector at 260 nm (nanometers)
Starting Delay: 0.00  Ending Retention Time: 12.00

| Peak Number | Retention Time | Area % |
|---|---|---|
| 1 | 1.52 | 0.0078 |
| 2 | 2.12 | 0.0060 |
| 3 | 2.63 | 0.2996 |
| 4* | 3.33 | 9.6187 |
| 5 | 4.77 | 0.4485 |
| 6† | 5.65 | 89.6195 |

*Ia
†Ib

The solid is a mixture predominated by the imminium salt form (4a; ir 1662 $cm^{-1}$) and the keto form (4b; ir 1710 $cm^{-1}$).

The (+) or (−) isomer of each of the compounds Ia and Ib are also the above invention. These are prepared by corresponding analogous procedures of the Example 1 appropriately using the individual +or − stereoisomers of pirmenol as starting material.

A preparative chromatographic scheme is described for the isolation of the pure stereoisomers or enantiomers of pirmenol from bulk racemic pirmenol as follows:

EXAMPLE 2

A chromatographic charge is prepared by completely dissolving 300 mg of racemic pirmenol in 3 mL of a solution of 75:25 hexane:2-propanol and warming to 65° C. 100 µL of this solution is injected onto a 500×20.0 mm Chiralcel OJ ® preparative column (Diacel Chemical Industries, Tokyo, Japan). This charge is chromatographed over the support with 99:1 hexane:2-propanol at a flow rate of 9.5 mL/min. The column and injector are jacketed in a CH-460 column heater (Fiatron Laboratory Systems, Oconomowoc, WI) at a constant temperature of 55° C. The eluate is monitored by measuring its ultraviolet absorbance at 254 nm.

The first major ultraviolet absorbing fraction is the (+) enantiomer, cis-(+)-α-[3-(2,6-dimethyl-1-piperidinyl)propyl]-α-phenyl-2-pyridinemethanol. The capacitance factor k' for this enantiomer is approximately 0.9 (90 mL) and is designated as "solution A". The value for the capacitance factor k' is given by the expression $k'=(V_e-V_o)/V_o$ where $V_o$ is the void volume, 170 mL, and $V_e$ is the volume of mobile phase eluted at the maximum ultraviolet absorbance of the first (+) enantiomer, i.e., cis-(+)-α-[3-(2,6-dimethyl-1-piperidinyl)propyl]-α-phenyl-2-pyridinemethanol. The second major ultraviolet absorbing fraction is the (−) enantiomer, cis-(−)-α-[3-(2,6-dimethyl-1-piperidinyl)propyl]-α-phenyl-2-pyridinemethanol. This component elutes at a k' of 1.7 (160 mL) and is designated as "solution B". An intermediate fraction eluting at a k' of 1.6 (20 mL), which corresponds to the ultraviolet minimum between the two enantiomers contains approximately equal parts of each enantiomer.

This preparative procedure is repeated an additional 23 times. All the "solution A" fractions are combined and concentrated in vacuo to a dried film with a rotary evaporator. This film is scraped from the sides of the round-bottom rotary evaporator flask. The solid is collected and weighed. The resulting 134 mg of cis-(+)-α-[3-(2,6-dimethyl-1-piperidinyl)propyl]-α-phenyl-2-pyridinemethanol i.e., (+)pirmenol, is found to be 98% enantiomerically pure by high performance liquid chromatography using the conditions listed in Table 1. The 23 fractions labeled "solution B" are combined and dried as described for the "solution A" fractions. The resulting 110 mg of solid, cis-(−)-α-[3-(2,6-dimethyl-1-piperidinyl)propyl]-α-phenyl-2-pyridinemethanol i.e., (−)pirmenol, is found to be 98% enantiomerically pure by high performance liquid chromatography using the system described in Table 1. The physical properties of cis-(+)-α-[3-(2,6-dimethyl-1-piperidinyl)propyl]-α-phenyl-2-pyridinemethanol and cis-(−)-α-[3-(2,6-dimethyl-1-piperidinyl)propyl-α-phenyl-2-pyridinemethanol appear in Table 2.

TABLE 1

Column: Chiralcel OJ ® 4.6×250 mm 10 µm spherical particles
Mobile Phase: 99:1:0.1 hexane:2-propanol:diethylamine
Detection: 254 nm
Temperature: 70° C.
Injection Volume: 10 µL
Charge conc. 0.50 mg/mL in the mobile phase

TABLE 2

|  | cis-(+)-α-[3-(2,6-dimethyl-1-piperidinyl)-propyl]-α-phenyl-2-pyridinemethanol [(+)pirmenol] | cis-(−)-α-[3-(2,6-dimethyl-1-piperidinyl)-propyl-]α-phenyl-2-pyridinemethanol [(−)pirmenol] |
|---|---|---|
| Optical Rotation | $[å]_D = +1.08$ (c. 1.02 MeOH) | $[å]_D = -1.52$ (c. 0.99 MeOH) |
| Retention Volume Chiral HPLC | 4.8 mL | 5.4 mL |

We claim:
1. A compound of the formula (Ia)

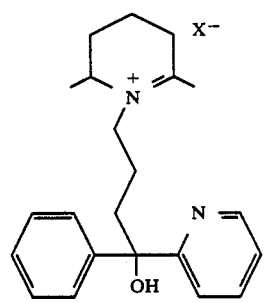

or its interconverting form (Ib)

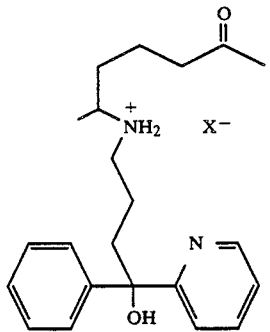

or mixtures thereof; individual stereoisomers and pharmaceutically acceptable acid addition salts thereof wherein X is a pharmaceutically acceptable anion.

2. The mixture of claim 1 which is an equilibrium of the compound of formula

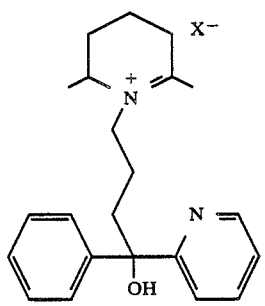

and the compound of the formula

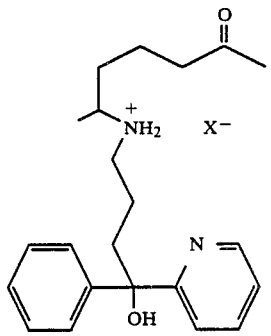

3. A compound of the formula Ia or Ib of claim 1 wherein X⁻ is acetate.

4. A mixture of the claim 2 wherein X⁻ is chloride.

5. A compound of the formula Ia or Ib of claim 1 wherein X⁻ is acetyl.

6. A mixture of the claim 2 wherein X⁻ is acetate.

7. A compound of the claim 1 which is the individual stereosiomer of Ia or Ib containing R or S carbinol carbon.

8. A mixture of claim 2 which is the individual stereoisomers of Ia and Ib containing the R carbinol carbon or the individual stereoisomers Ia and Ib containing the S carbinol carbon.

9. A compound of the formula Ia or Ib of claim 3 which is the hydrogen chloride salt of the compound.

10. A mixture of the claim 4 which is the hydrogen chloride salt of each of Ia and Ib in the mixture.

11. The pharmaceutical composition for treating arrhythmias in humans which comprises an antiarrhythmic amount of the formula Ia, Ib and mixtures thereof of the compound of claim 1, with a pharmaceutically acceptable carrier.

12. A method of treating arrhythmias in a human suffering therefrom comprising administering a compound of claim 1 of the formula Ia, Ib and mixtures thereof.

13. Cis-(−)-α-[3-(2,6-dimethyl-1-piperidinyl)propyl]-α-phenyl-2-pyridinemethanol.

14. Cis-(+)-α-[3-(2,6-dimethyl-1-piperidinyl)propyl]-α-phenyl-2-pyridinemethanol.

* * * * *

UNITED STATES PATENT AND TRADEMARK OFFICE
CERTIFICATE OF CORRECTION

PATENT NO. : 4,997,842

DATED : March 5, 1991

INVENTOR(S) : T. R. Hurley, et al

It is certified that error appears in the above-identified patent and that said Letters Patent is hereby corrected as shown below:

Column 16, line 17, change "acetate" to --chloride--.

Signed and Sealed this

Eighth Day of December, 1992

Attest:

DOUGLAS B. COMER

Attesting Officer    Acting Commissioner of Patents and Trademarks